(12) United States Patent
Liu

(10) Patent No.: US 9,107,641 B2
(45) Date of Patent: Aug. 18, 2015

(54) HEARTBEAT SYNCHRONIZED CARDIAC IMAGING

(71) Applicant: General Electric Company, Schenectady, NY (US)

(72) Inventor: James Zhengshe Liu, Salt Lake City, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 25 days.

(21) Appl. No.: 14/081,411

(22) Filed: Nov. 15, 2013

(65) Prior Publication Data

US 2015/0139388 A1  May 21, 2015

(51) Int. Cl.
 *A61B 6/00* (2006.01)
 *G06T 5/50* (2006.01)
(52) U.S. Cl.
 CPC .............. *A61B 6/541* (2013.01); *A61B 6/503* (2013.01)
(58) Field of Classification Search
 CPC ........ A61B 6/541; A61B 6/032; A61B 6/503;
   A61B 6/54; A61B 6/463; A61B 6/465;
   A61B 6/504; A61B 6/542; A61B 5/0456;
   A61B 5/0402; A61B 5/0464; A61B 5/721;
   G06T 5/50; G06T 7/0012
 USPC ............... 378/8, 95, 19, 110, 4, 62; 382/131; 600/509
 See application file for complete search history.

(56) References Cited

U.S. PATENT DOCUMENTS

| | | | | |
|---|---|---|---|---|
| 4,747,118 | A * | 5/1988 | Spaak | 378/110 |
| 6,236,705 | B1 * | 5/2001 | Stergiopoulos et al. | 378/8 |
| 6,275,560 | B1 * | 8/2001 | Blake et al. | 378/8 |
| 6,324,254 | B1 * | 11/2001 | Pflaum | 378/95 |
| 6,438,196 | B1 * | 8/2002 | Cesmeli | 378/8 |
| 6,639,965 | B1 * | 10/2003 | Hsieh et al. | 378/8 |
| 7,313,213 | B1 * | 12/2007 | Hsieh et al. | 378/8 |
| 8,233,682 | B2 * | 7/2012 | Fessler et al. | 382/128 |
| 2007/0255150 | A1 * | 11/2007 | Brodnick | 600/509 |
| 2008/0063137 | A1 * | 3/2008 | Hsieh et al. | 378/8 |
| 2008/0123812 | A1 * | 5/2008 | Sabol et al. | 378/95 |
| 2008/0243018 | A1 | 10/2008 | Zuhars et al. | |
| 2008/0287778 | A1 * | 11/2008 | Li et al. | 600/424 |
| 2008/0300478 | A1 | 12/2008 | Zuhars et al. | |
| 2009/0129661 | A1 * | 5/2009 | Licato | 382/134 |
| 2010/0056897 | A1 * | 3/2010 | Zhang | 600/407 |
| 2011/0044524 | A1 * | 2/2011 | Wang et al. | 382/131 |
| 2013/0190637 | A1 * | 7/2013 | Zhang et al. | 600/521 |
| 2014/0098932 | A1 * | 4/2014 | Profio et al. | 378/19 |
| 2014/0133622 | A1 * | 5/2014 | Yin et al. | 378/8 |
| 2014/0254762 | A1 * | 9/2014 | Yamato et al. | 378/62 |

* cited by examiner

*Primary Examiner* — David A Vanore
(74) *Attorney, Agent, or Firm* — McAndrews, Held & Malloy, Ltd.; William Baxter

(57) ABSTRACT

This disclosure presents systems and methods that synchronize an x-ray imaging system with the heartbeat of a patient. A patient's heartbeat is sensed with a cardiac monitoring unit, and a processing unit generates x-ray pulses that are synchronized with the patient's heartbeat. Based on the real-time heartbeat information, an x-ray imaging device can be operated to obtain x-ray images at various states of the cardiac cycle. The x-ray images taken over several cardiac cycles can be combined based on the relative state of the cardiac cycle in which the images were obtained to achieve high temporal resolution of a cardiac cycle. Additionally, x-ray images obtained at common relative states of the cardiac cycle can be combined to provide higher quality cardiac image or images.

20 Claims, 8 Drawing Sheets

HEARTBEAT SYNCHRONIZED CARDIAC IMAGING

CROSS REFERENCE TO RELATED APPLICATIONS

[Not Applicable]

BACKGROUND OF THE INVENTION

A useful x-ray image can often be the product of assembling multiple x-ray images or image frames obtained over the course of a period of time. Information from each x-ray image can be combined to generate one or more overall x-ray images that yield a more detailed picture of the imaged object. However, any movement or displacement of the imaged objects during the collection of x-ray images can result in blurring, distortions, defects, or other imperfections in the resulting x-ray image.

For human patients that are the object of an x-ray image scan, small movements of the body during an x-ray scan can negatively affect the imaging process. For example, motion caused by breathing during an x-ray scan can result in a blurred or distorted x-ray image. However, because an imaging process is relatively short, a patient can typically be asked to hold their breath during the imaging process to avoid these issues. Other movements of the human body, however, are involuntary. For example, a patient cannot voluntarily stop their heart from beating. Accordingly, it can be difficult to obtain x-ray images of a human heart without obtaining image distortions caused by the motion effect.

Moreover, because a healthy heart is always beating, the size, shape, and appearance of the heart are constantly changing. Accordingly, it can be valuable for a medical practitioner to obtain information about a heart at various specific states or stages of a heartbeat, or cardiac cycle. However, due to the constant movement of the beating heart, capturing x-ray images at any specific state or stage of the cardiac cycle can be difficult.

BRIEF DESCRIPTION OF THE INVENTION

Certain embodiments of the present technology provide heartbeat synchronized imaging systems. In certain embodiments, the system comprises an x-ray imaging device. The x-ray imaging device can be configured to acquire x-ray images by generating a series of x-ray pulses. Certain embodiments also include a cardiac monitoring unit configured to obtain heartbeat information relating to the cardiac cycle of a patient. The system can also include a data storage device operable to store x-ray images obtained by the x-ray imaging device. In certain aspects, the system includes a user interface that is configured to allow a user to operate at least one of the x-ray imaging device, the cardiac monitor unit, and the data storage device. The system can also comprise a processing unit that is communicatively coupled to the x-ray imaging device, the cardiac monitor unit, the data storage device and the user device. The processing unit can be configured execute a synchronization application that generates at least one synchronized pulse rate based on the heartbeat information of the patient. The processing unit can also be configured to execute an imaging application that operates the x-ray imaging device at the at least one synchronized pulse rate across a plurality of cardiac cycles to obtain x-ray images. In some aspects, the processing unit is also configured to execute an image combination application that combines x-ray images to generate cardiac cycle images.

Some embodiments of the present technology provide methods for generating cardiac cycle x-ray images. The method can include the step of monitoring a heartbeat to obtain heartbeat information. The heartbeat can be defined, for example, by a repeating cardiac cycle. The method can also include the step of generating a first series of x-ray pulses during a first cardiac cycle to obtain a first set of x-ray images. Some embodiments include the step of generating at least one additional series of x-ray pulses during at least one subsequent cardiac cycle to obtain at least one additional set of x-ray images. In certain aspects, the method includes the step of combining the first set of x-ray images and the at least one additional set of x-ray images to obtain a cardiac cycle x-ray image. In some aspects of the present technology, each series of x-ray pulses are configured based on the heartbeat information. And in some embodiments, each x-ray pulse can generate an x-ray image at a relative state of the cardiac cycle.

Certain embodiments of the present technology provide a non-transitory computer-readable medium encoded with a set of instructions for a computer. The instructions can include a first routine that is configured to obtain heartbeat information. The heartbeat can be defined, for example, by a repeating cardiac cycle. In some aspects, the instructions include a second routine configured to generate a series of x-ray pulses during a plurality of cardiac cycles, each pulse of the series of x-ray pulses configured to occur at a relative state of the cardiac cycle. In certain embodiments, a third routine is configured to adjust the relative states of the cardiac cycle at which each x-ray pulse is generated.

Figure 1:
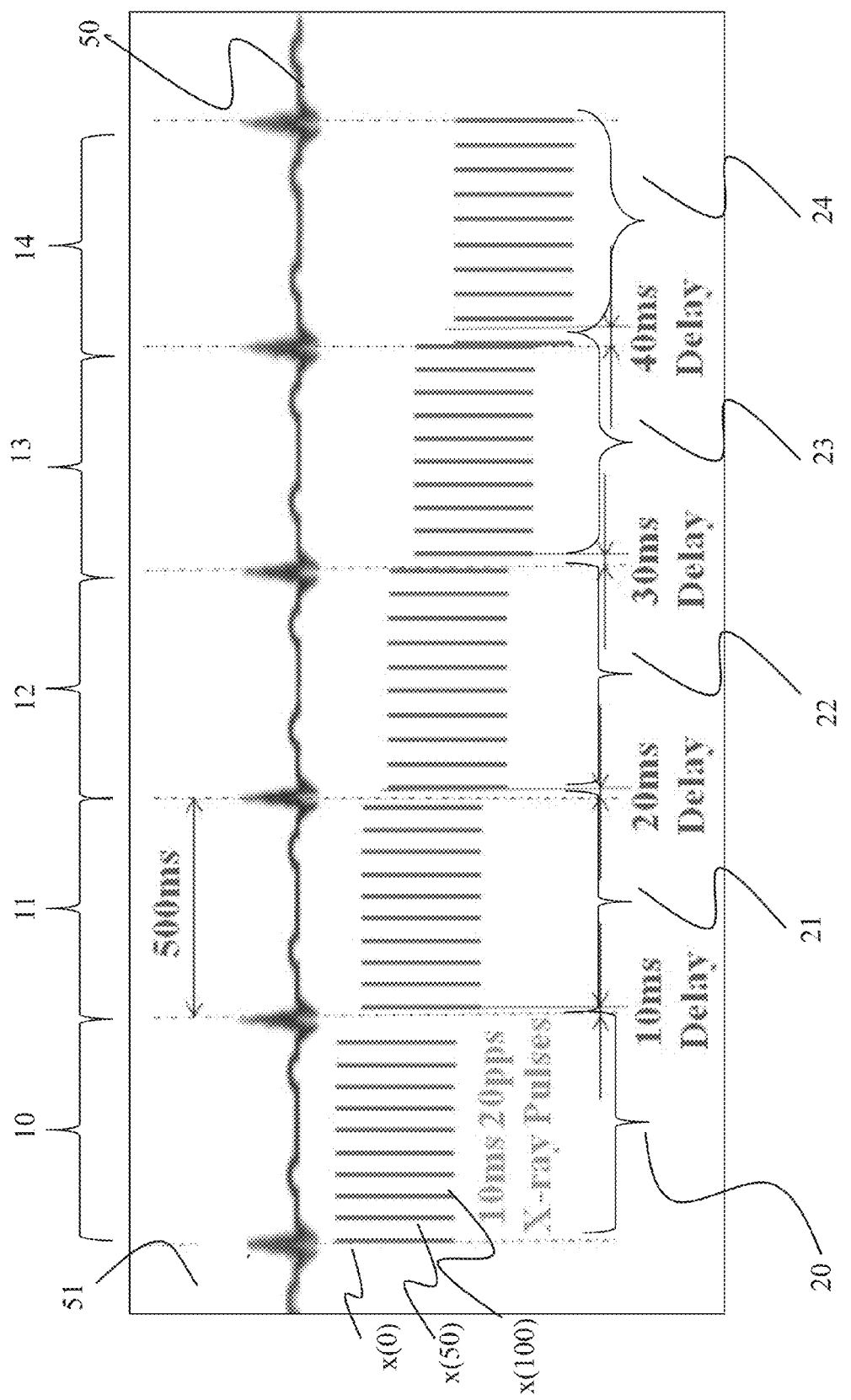
FIG. 1 is a graph depicting a heartbeat reading and various x-ray pulses obtained over time in accordance with at least one embodiment of the present technology.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE INVENTION

The present technology relates to x-ray imaging. More specifically, the present technology provides methods and systems that synchronize an x-ray imaging device with the heartbeat of the imaged patient. That is, the present technology provides systems and methods that monitor the heartbeat of the patient and adjust the x-ray pulses so that the pulses correspond with the patient's heartbeat. In this manner, x-ray images acquired across multiple cardiac cycles can be combined to provide enhanced and/or more detailed x-ray images.

The heart is a difficult body part to image. Because the heart is always beating, there is no "at rest" state at which the heart can be carefully imaged in a simple manner. Moreover, because the imaging process can take time, the resulting cardiac x-ray images can be blurry or lack the detail and resolution necessary to provide useful results.

Patients may be able to hold their breath for a short period of time during x-ray imaging to avoid motion effect issues during x-ray scans of many parts of the body. However, patients cannot control, or voluntarily stop their heartbeats. Accordingly, any x-ray imaging of the heartbeat must take into consideration that the heart is always beating at a relatively rapid rate.

In order to reduce motion effect in cardiac imaging, cardiac x-rays typically employ very narrow (i.e., short in duration) x-ray pulses, operating at a very high pulse rate. However, generating quality and useful cardiac x-ray images can be very difficult. One way to obtain quality cardiac x-ray images could involve using cardiac x-ray systems powerful enough to expose sufficient x-rays during the relatively short pulse period. That is, employing imaging systems with an increased potential (e.g., kV) or amperage (e.g., mA) to increase the number of photons generated over time. However, to the extent that x-ray equipment is capable of delivering kV or mA necessary to obtain quality images with a short pulse duration are available, they are very rare and expensive, and indeed, not practical. Moreover, these x-ray pulses need to be generated relatively quickly, which can be especially challenging, for example, for a mobile c-arm x-ray system.

Additionally, in order to diagnose cardiac diseases, doctors may occasionally need to observe an entire cardiac cycle. To observe such a cardiac cycle, x-ray imaging system need to operate at a high pulse rate so that image frames can be frequently generated at many relative states of the cardiac cycle. That is, a useful series of cardiac images will have a high resolution (i.e., number of frames per cardiac cycle), so that a practitioner can readily observe the heart at all states of a cardiac cycle.

The present disclosure provides systems and methods that overcome the limitations of the current state of the art by synchronizing x-ray pulses with the heartbeats of a patient. This allows for the x-ray images to be collected over the course of multiple cardiac cycles. In this manner, the present technology can be used to control the timing of each pulse so that it occurs at a specific moment or relative state of a cardiac cycle, and then combine the images acquired over the course of multiple cycles.

By controlling the timing in each of the cycles, the present technology can achieve high temporal resolution with less powerful generator and/or slower pulse rate x-ray imaging systems. These principles can also be used, for example, to eliminate motion effect in cardiac vascular imaging.

As noted above, it can be valuable to have available a series of x-ray images over an entire cardiac cycle. Typically, this process would involve an x-ray imaging system operating at a very high pulse rate. For example, in order to carefully observe an entire cardiac cycle, it may be necessary to provide as many as 50 image frames of the heart during a cardiac cycle. In this manner, each frame can provide an x-ray image of the heart at a specific moment in time, or a relative state of the cardiac cycle. In such an example, if the heart of a patient beats at 120 times per minute, the x-ray imaging system would have to generate 100 pulses per second (PPS) in order to achieve the temporal resolution of 50 images per cardiac cycle. This high rate would be challenging to meet even for the most sophisticated and expensive equipment.

The present technology provides heartbeat synchronized imaging systems and methods that realize high temporal resolution with systems that have a significantly slower pulse rate. For example, the present technology allows an imaging system that is only capable of generating 20 PPS to generate cardiac x-ray images having a resolution equivalent to 100 PPS.

These results are achieved by acquiring images over multiple cardiac cycles, while setting different amount of time delays in each cycle. For example, images can be obtained over five, ten, or fifteen cardiac cycles, with each x-ray pulse occurring at different relative states of the cardiac cycle. In this manner, a patient may only need to hold his or her breath for a brief time while the imaging process observes a few cardiac cycles.

In some aspects of the present technology, multiple series of x-ray pulses are generated over multiple series of heartbeats or cardiac cycles. In certain aspects, each series can be different from one another so that each x-ray pulse occurs at a different moment, or relative state of the cardiac cycle. The pulses of the various cycles can then be combined to generate an x-ray image sequence at a higher pulse rate than the x-ray imaging device is otherwise capable of generating.

For example, an imaging system can be synchronized with a patient's heartbeat and configured to generate a certain number of pulses per cardiac cycle, for example, ten pulses per cycle. The system can then be configured to generate ten images per cycle over the course of five cardiac cycles to gather a total of 50 images throughout the cardiac cycle. In such an embodiment, where a heart rate is 120 beats per minute, the pulses can be configured to occur 50 ms apart so that 10 pulses are generated per each cardiac 500 ms cardiac cycle.

In some embodiments, series of x-ray pulses can be generated over successive cardiac cycles. For example, x-ray pulses can be generated over five to ten cardiac cycles. The pulses of each cardiac cycle can be configured so that each pulse occurs at a different relative state of the cardiac cycle. That is, the x-ray pulses of successive cardiac cycles can be configured to be delayed or offset from the first series of pulses.

During the first cardiac cycle, a series of pulses can be taken such that the first pulse of the series is synchronized with a relative state of the heartbeat, for example, the peak of the heartbeat. During the second cardiac cycle, another series of x-ray pulses can be generated at the same pulse rate, with a delay or time offset such that the first pulse of the second series is delayed with respect to the peak of the heartbeat. For example, the first pulse of the second series can be configured to occur at a state of the cardiac cycle 10 ms after the peak. Similarly, each successive series of pulses can be delayed or offset to occur at a new moment or relative state of the cardiac cycle. In this manner, several series of pulses can be configured so that one pulse is taken at each of a predetermined number of states during the cardiac cycle.

FIG. 1 is a graph demonstrating an example operation of an imaging system synchronized with a patient's heartbeat. More specifically, FIG. 1 is a graph depicting a heartbeat reading 50 and various series of x-ray pulses (20, 21, 22, 23, and 24) obtained over time. The heartbeat reading 50 can be monitored, for example, by an electrocardiogram ("ECG"). In FIG. 1, the heartbeat reading depicts a heart rate of about 2 beats per second. That is, each cardiac cycle (or heartbeat cycle) is approximately 500 ins in duration. As shown in FIG. 1, several series x-ray pulses (20, 21, 22, 23, and 24) are generated over each of five successive cardiac cycles (10, 11, 12, 13, and 14) at a pulse rate of 20 PPS, or one pulse per 50 ms. In the embodiment depicted by FIG. 1, each x-ray pulse has a pulse duration of 10 ms. That is, each x-ray pulse lasts 10 ms.

In the embodiment of FIG. 1, each successive series of x-ray pulses is delayed with respect to one another, in terms of the relative state of the cardiac cycle. For example, the first series of pulses 20 are configured such that the first x-ray pulse is synchronized with the peak 51 of the first cardiac cycle 10. The second series of pulses 21 is configured such that the first pulse is delayed 10 ms from the peak 51 of the second cardiac cycle 11. Likewise, the first pulses of the third series 22, the fourth series 23, and the fifth series 24, are configured to occur with delays of 20 ms, 30 ms, and 40 ms, respectively, from the peaks of the cardiac cycles 12, 13, and 14. In this manner, 50 x-ray pulses can be generated over the course of five cardiac cycles, such that each pulse occurs at a different relative state of the cardiac cycle. These images can be combined to generate a high temporal resolution image of a cardiac cycle.

Accordingly, FIG. 1 demonstrates an x-ray imaging system that can generate x-ray images having a temporal frame rate of 50 frames per cardiac cycle. Using the present technology, the images can be combined, for example, using a computer processor, to generate a series of x-ray images. For example, in this particular example, 10 images per cardiac cycle are acquired. The first ten images obtained during the first series of pulses 20 of the first cardiac cycle 10 are represented as:
{x(0), x(50), x(100), x(150), x(200), x(250), x(300), x(350), x(400), x(450)};
where each x(i) corresponds to an x-ray pulse generated at a time of i ms after the peak 51 of the cardiac cycle, such that each x corresponds to the time instant of 0 ms, 50 ms, 100 ms, 150 ms, 200 ms, 250 ms, 300 ms, 350 ms, 400 ms, and 450 ms, respectively, after the peak of the heartbeat reading (e.g., an ECG). Because the system of the exemplary embodiment operates at 20 PPS, the time duration between any 2 consecutive images is 1000 ms/20 PPS=50 ms.

As indicated, the images collected during the 2nd through the 5th cardiac cycles (i.e. series 21-24 obtained during cycles 11-14), are acquired with time delay of 10 ms, 20 ms, 30 ms, and 40 ms, respectively, to the peak of the ECG signal. Thus the images are represented as:
{x(10), x(60), x(110), x(160), x(210), x(260), x(310), x(360), x(410), x(460)};
{x(20), x(70), x(120), x(170), x(220), x(270), x(320), x(370), x(420), x(470)};
{x(30), x(80), x(130), x(180), x(230), x(280), x(330), x(380), x(430), x(480)}; and
{x(40), x(90), x(140), x(190), x(240), x(290), x(340), x(390), x(440), x(490)}.

By rearranging the order of the images according to the relative delay from the peak of the ECG signal, a matrix of 5× high temporal resolution images can be obtained, as indicated by:
{x(0), x(10), x(20), x(30), x(40), x(50), x(60), . . . , x(450), x(460), x(470), x(480), x(490)}.

That is, a matrix of images can be obtained such that there is one image per ever 10 ms of the cardiac cycle. It should be understood that the present technology should not be limited by the example depicted in FIG. 1. In some embodiments, more or less, images can be obtained per cardiac cycle. For example, in some embodiments, five, fifteen, or twenty images can be obtained per cardiac cycle, depending on the heart rate of the patient, the desired temporal resolution of the x-ray images, the pulse duration, and the number of cardiac cycles over which the imaging process occurs.

Figure 2:
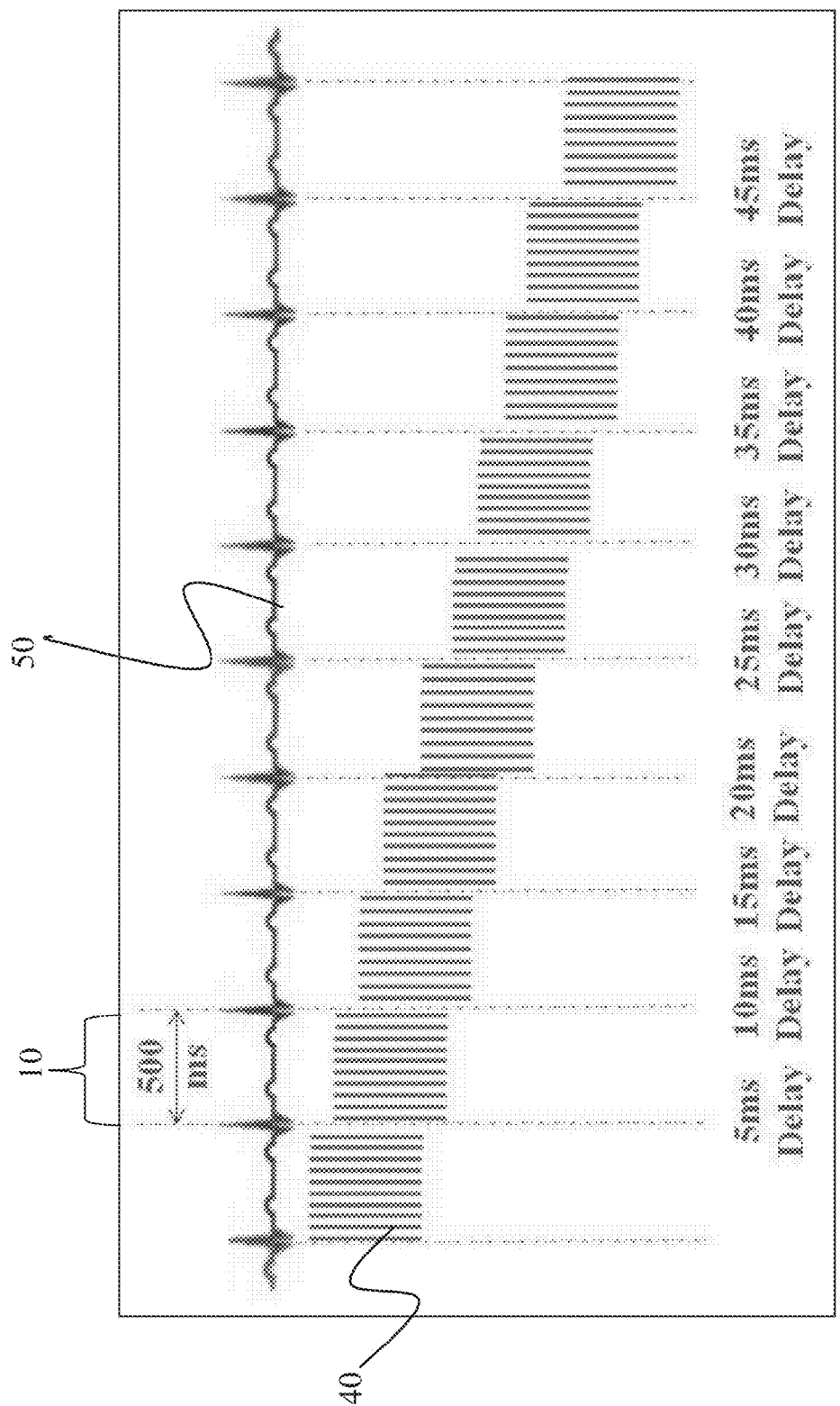
FIG. 2 is another graph depicting a heartbeat reading and various x-ray pulses obtained over time in accordance with at least one embodiment of the present technology.
Figure 3:
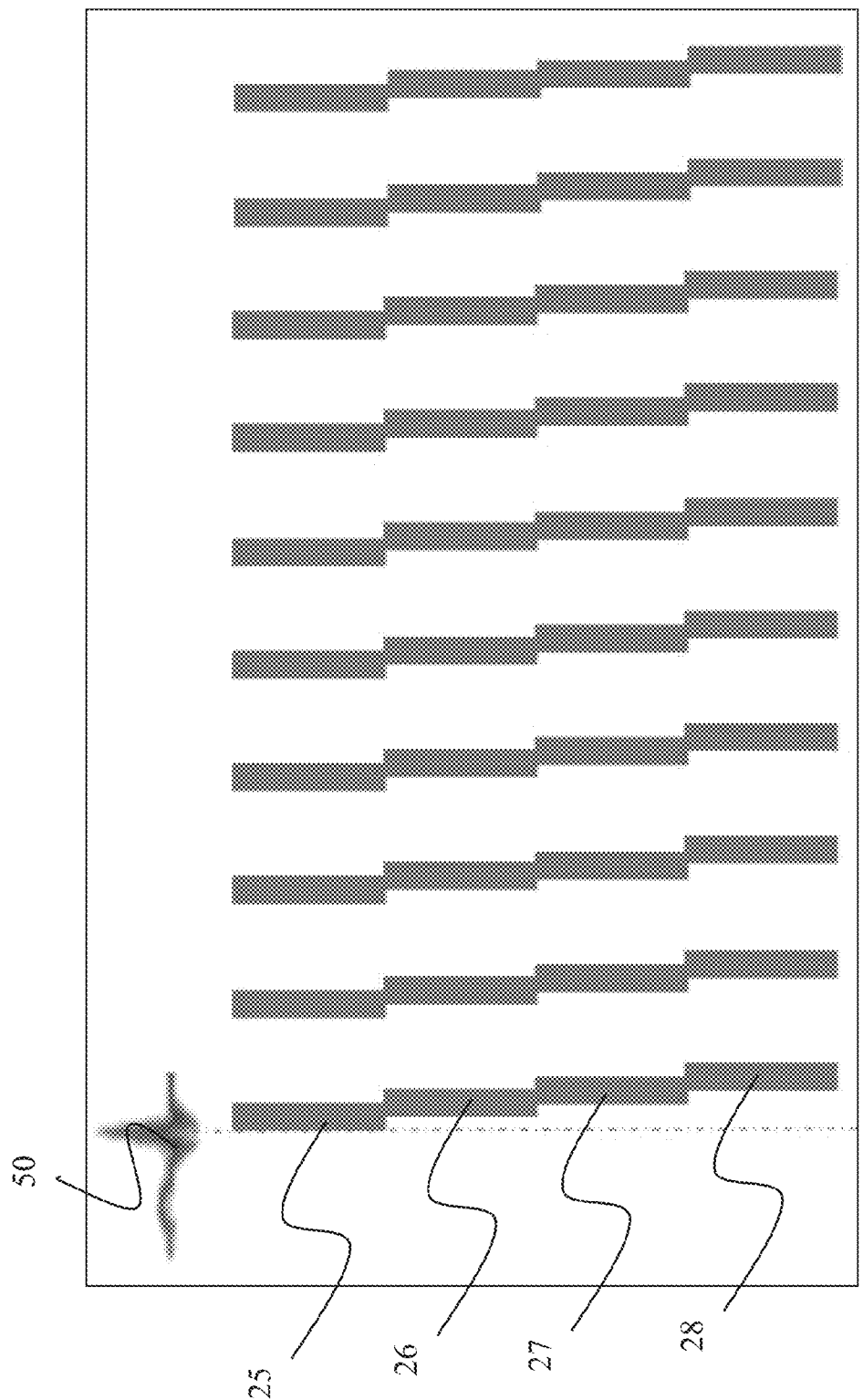
FIG. 3 is a graph depicting various x-ray pulses overlapping with respect to relative states of the cardiac cycle in accordance with at least one embodiment of the present technology.

In some embodiments, higher temporal resolution can be achieved by overlapping the x-ray pulses in more cardiac cycles. FIGS. 2 and 3 are graphs depicting an example of such an embodiment.

FIG. 2 shows heartbeat reading 50 and multiple series of x-ray pulses 40 obtained over time over the course of several cardiac cycles 10. In FIG. 2, the heart rate is again 120 beats per minute, resulting in a cardiac cycle of 500 ms. Each x-ray pulse in the FIG. 2 embodiment has a duration of 10 ms and is obtained at a pulse rate of 20 PPS. And each successive series of x-ray pulses is delayed by 5 ms from the previous series.

Because the x-ray pulses in the FIG. 2 example have a duration of 10 ms, and a delay from one cycle to the next of 5 ms, the x-ray pulses will overlap. That is, one 10 ms pulse will overlap by 5 ms with another pulse obtained during another cardiac cycle.

FIG. 3 is a graph depicting various series of x-ray pulses 25, 26, 27, and 28 overlapping with respect to relative states of the cardiac. As shown, each pulse has a duration that overlaps with at least one other pulse obtained during another cardiac cycle. In this manner, it is possible to achieve resolutions of 100 images per cardiac cycle at heart rate of 120 beats per second, which corresponds to 200 images per second.

The present technology has been described in terms of an embodiment that provides for higher temporal resolution of x-ray images by providing multiple series of x-ray pulses that are delayed with respect to one another. Some embodiments of the present technology can use the synchronization feature to generate x-ray pulses that occur at the same relative states of a cardiac cycle. In this manner, multiple x-ray images can be combined to take advantage of a shorter x-ray pulse.

X-ray images resulting from x-ray pulses can be assembled by taking the average of the x-ray image over the duration of the pulse. However, the longer the x-ray pulse, the more movement of the imaged object will occur. Accordingly, the averaged resulting image will be more blurry the longer the duration of the x-ray pulse.

For these and other reasons, it can be desirable to use narrow x-ray pulses (i.e., x-ray pulses with a relatively short pulse duration) in cardiac imaging systems as a way to limit the amount of heart movement occurring during the duration of the x-ray pulse. However, using narrow pulses can have some weaknesses. For example, the narrower the x-ray pulse, the less dose can be generated during the pulse. As a result, the image quality and level of detail obtained by the x-ray pulse is reduced.

The presently disclosed heartbeat synchronized imaging technology can be applied to overcome these and other shortcomings. For example, x-ray pulses can be configured to occur at the same moments, or relative states of the respective cardiac cycle. That is, several series of cardiac images can be configured to occur at predetermined relative states of the cardiac cycle so that the acquired images can be combined to depict the heart at the shared cardiac cycle state. This ability to combine cardiac images allows for x-ray pulses to have a shorter duration (thereby resulting in a less blurry image), without sacrificing the quality and detail of the resultant image.

Figure 4:
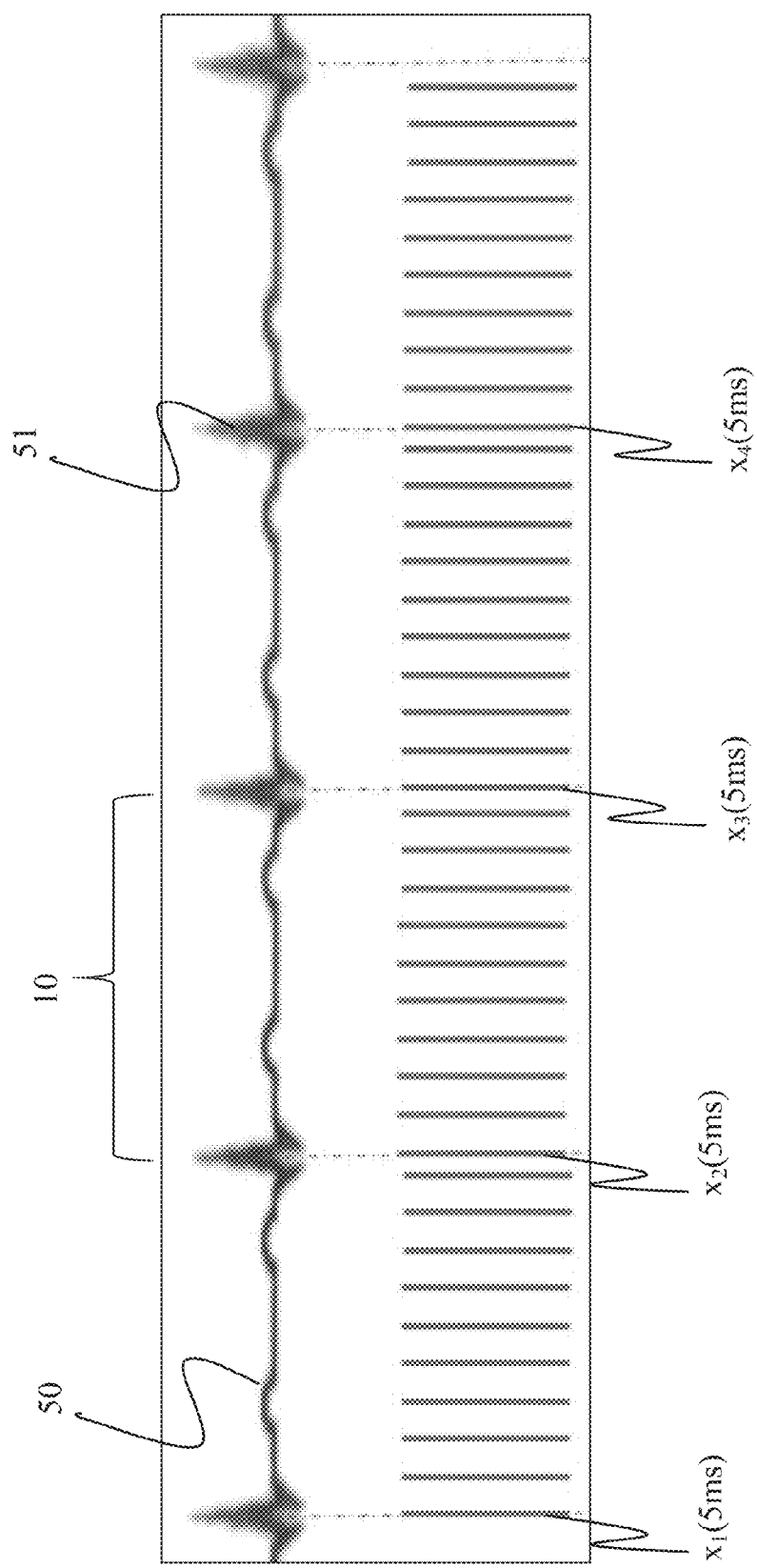
FIG. 4 is a chart depicting a heartbeat reading synchronized with an x-ray pulse rate such that the x-ray pulses occur at the same relative states of the cardiac cycle in accordance with at least one embodiment of the present technology.

FIG. 4 depicts an example of an exemplary embodiment of x-ray image pulses (synchronized to occur at the same relative states of the cardiac cycle 10. As shown in FIG. 4, each x-ray pulse (e.g., $x_1$, $x_2$, $x_3$, and $x_4$) is synchronized with the heartbeat 50 so that multiple images acquired corresponding to the same relative cardiac state can be combined together to overcome the mA limitation of the imaging system.

For example, let $x_1$(5 ms), $x_2$(5 ms), $x_3$(5 ms), and $x_4$(5 ms)

be the 4 images acquired in different cardiac cycles but at the same relative state of the cardiac cycle, 5 ms after the heartbeat peak 51. Accordingly, $$x(5\ ms) = x_1(5\ ms) + x_2(5\ ms) + x_3(5\ ms) + x_4(5\ ms)$$

will represent an equivalent to one image acquired at the same relative time instant with 4×mA. That is, the four images acquired 5 ms after the peak 51 can be combined to obtain one combined image x(5 ms) representing the relative state of the heart 5 ms after the heartbeat peak. In this manner, several x-ray pulses of shorter duration can be executed to generate an accumulated x-ray image that is not blurry yet maintains a high quality as a result of the added mA.

FIG. 4 depicts an example where images from four successive cardiac cycles are combined to generate an accumulated x-ray image. In some embodiments, the images can be accumulated over more or less cardiac cycles in order to achieve the desired image quality.

In some embodiments, the images can be accumulated by the following formula:

$$y(k) = \frac{1}{k} x(k) + \frac{k-1}{k} y(k-1);$$

where x(k) is the $k^{th}$ image acquired for the same relative cardiac state; and y(k) is the resulting image accumulated form the corresponding k images obtained.

In this manner, the accumulation and the image acquisition can stop when the accumulated image y(k) is of a desired image quality.

Certain embodiments of the present technology also allow for a medical practitioner to select a relative state of the cardiac cycle to image. For example, in diagnosing cardiac diseases, a doctor may need to observe the x-ray image at a specific state of the cardiac cycle, for instance, the moment at the peak of the ECG signal.

The presently disclosed heartbeat synchronized cardiac imaging systems and methods allow for this need to be met by, for example, acquiring fluoroscopic images with very narrow x-ray pulse at a pulse rate of 1 pulse per cardiac cycle. The x-ray pulses are controlled to be at the same state relative to the peak of the heartbeat, or ECG signal.

Figure 5:
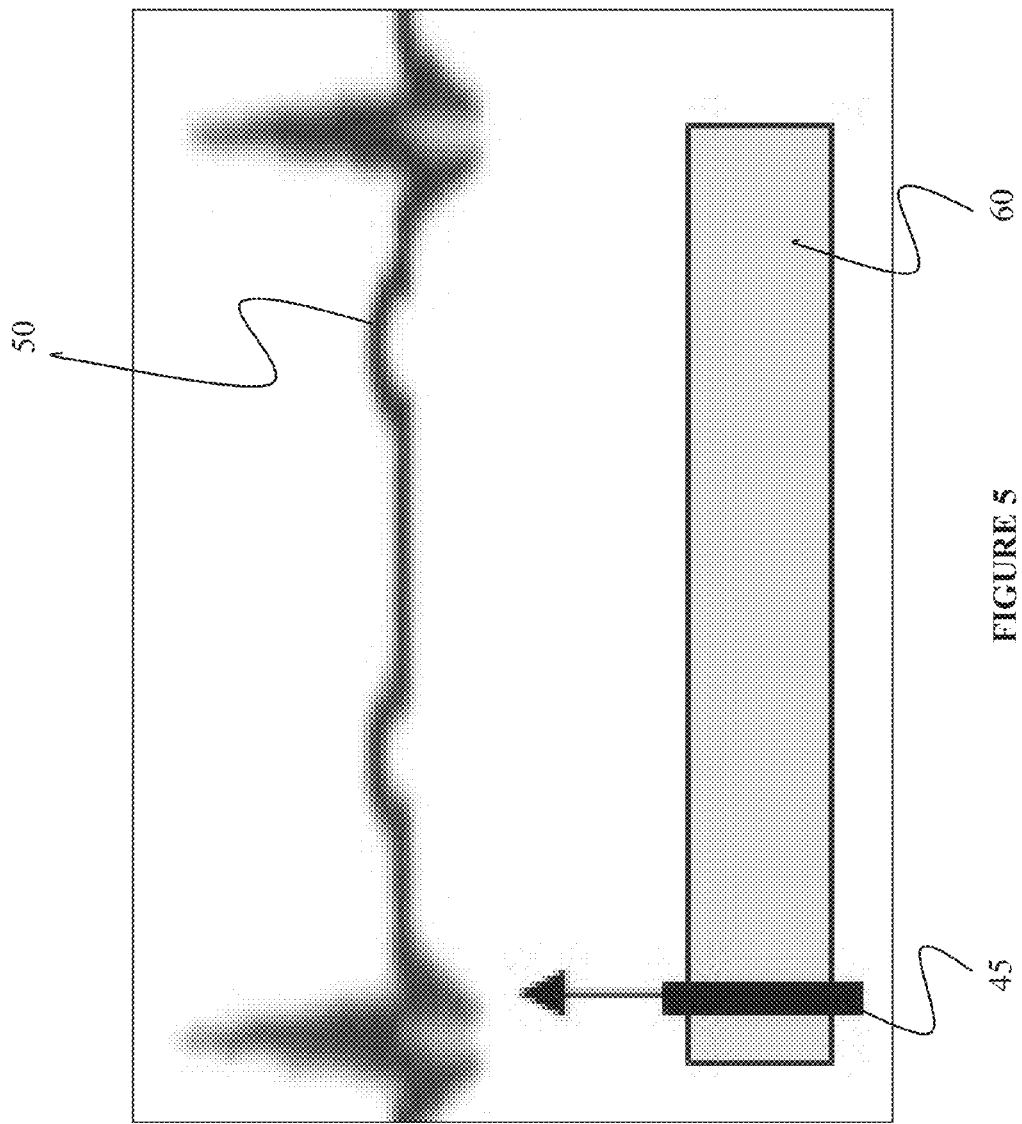
FIG. 5 shows a heartbeat reading in connection with a user controlled cardiac state selection slider in accordance with at least one embodiment of the present technology.

FIG. 5 shows a heartbeat reading 50 in connection with a user controlled cardiac state selection slider 60 bar. In this manner, a user can select an exact moment of the cardiac cycle to observe by sliding a timing control slider 45 to a point corresponding with the relative state of the cardiac cycle. Accordingly, the system can adjust the timing of the x-ray pulse relative to the heartbeat signal 50. In this manner, the doctor can view any desired relative state of the cardiac cycle.

Figure 6:
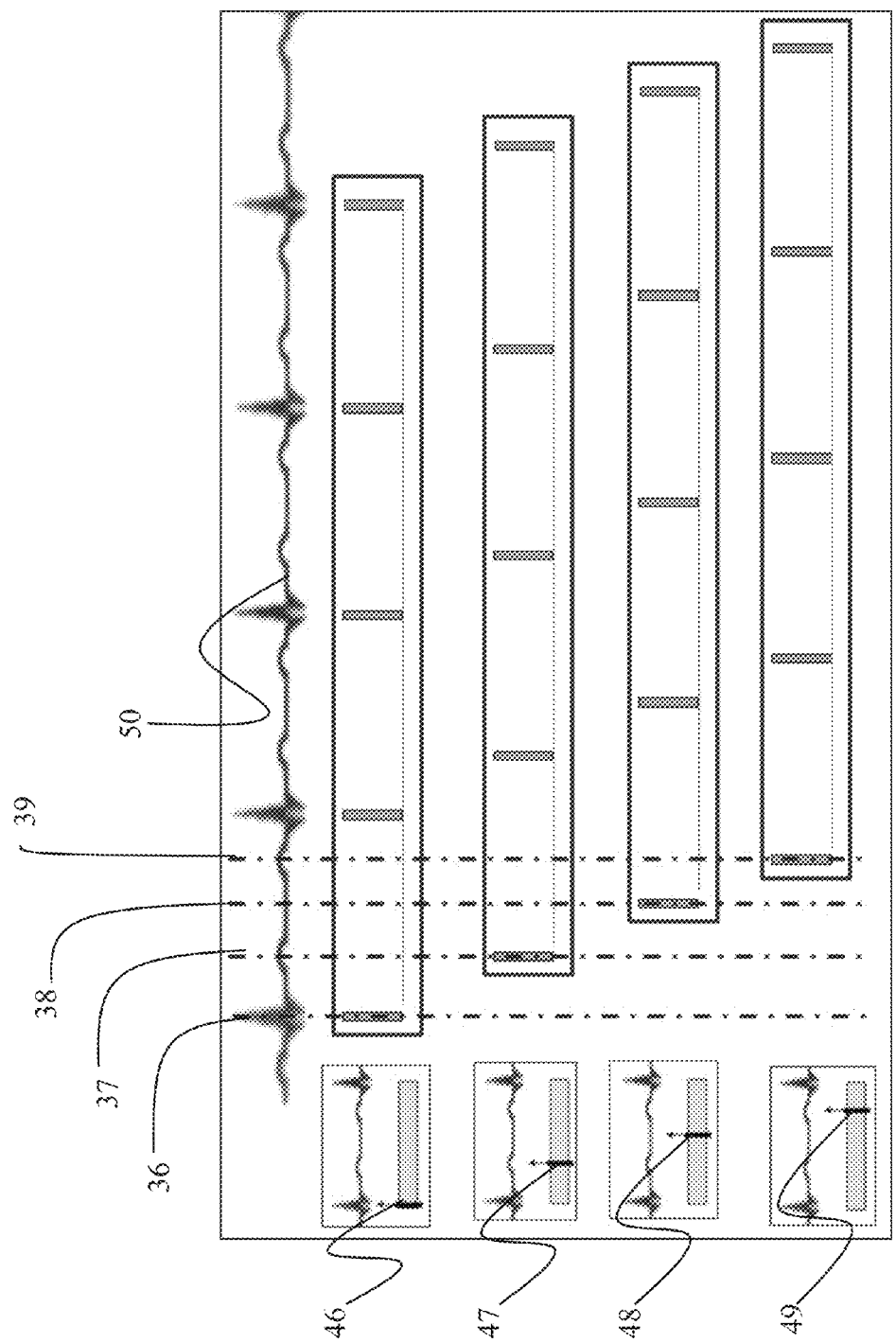
FIG. 6 is a diagram depicting a heartbeat reading and x-ray pulses occurring at user-selected relative states of the cardiac cycle in accordance with at least one embodiment of the present technology.

FIG. 6 is a diagram depicting a heartbeat reading 50 and x-ray pulses (36, 37, 38, and 39) occurring at user-selected relative states (46, 47, 48, and 49) of the cardiac cycle. For example, in the first line, a user has selected, via a control slider, a pulse to occur at a relative state 46, which corresponds to the peak 36 of the cardiac cycle. As such, the present technology can generate several successive (e.g., five) x-ray pulses that correspond with the peak 36 of the cardiac cycle, and combine these images to form an accumulated cardiac image at the peak of the cardiac cycle.

Similarly, in the second line, a user selection 47 corresponds with a pulse occurring at a relative state 37 about one third of a way through the cardiac cycle. Likewise, user selections 48 and 49 correspond with pulses being generated at relative states 38 and 39 of the cardiac cycle. In each instance, the present technology can generate several successive (e.g., five) x-ray pulses that correspond with the corresponding states of the cardiac cycle, and combine the images to form an accumulated cardiac image.

In order to reduce image noise, the displaying images can be accumulated over multiple of cardiac cycles with a temporal filter. In some embodiments, the images can be accumulated using the filtering formula:

$$y_{i,j}^{\{k\}} = (1-\alpha) x_{i,j}^{\{k\}} + \alpha y_{i,j}^{\{k-1\}}$$

where:

$\alpha$ is a filtering parameter in the range of (0, 1), and can be selected by the user;

$x_{i,j}^{\{k\}}$ is the $k^{th}$ image (i.e., the pixel value at pixel coordinate (i,j)) acquired for the same cardiac state; and $y_{i,j}^{\{k\}}$ is the resulting image (i.e., the pixel value at pixel coordinate (i,j)) accumulated form the corresponding k images.

In this manner, when:

$$\alpha = \frac{k-1}{k};$$

the filter formula becomes:

$$y_{i,j}^{\{k\}} = \frac{1}{k} x_{i,j}^{\{k\}} + \frac{k-1}{k} y_{i,j}^{\{k-1\}}$$

which is the average of the n incoming image frames.

It should be appreciated, however, that other embodiments of the present technology can employ alternative filtering formulas to generate the accumulated x-ray images.

There are many other applications that can take advantage of the present technology. For example, by synchronizing the x-ray pulse to the heartbeats of the patient, digital subtraction angiography (DSA) can be taken to reduce the motion effect of the heart in the subtracted cardiac vascular images.

The DSA imaging process can involve two steps. First, the anatomy is imaged without use of a contrast agent. The contrast agent is then injected to the blood vessel of the patient and the patient is imaged again. In this manner, the difference between images obtained with and without contrast agent can represent the contrast agent on the blood vessel without the background anatomy, which can then be used to determine if and where a blood vessel is congested.

By applying the present technology, a set of background images can be acquired at the certain states of the cardiac cycle, and other sets contrast agent images can be obtained at the same states to eliminate the effect of heart movement.

Figure 7:
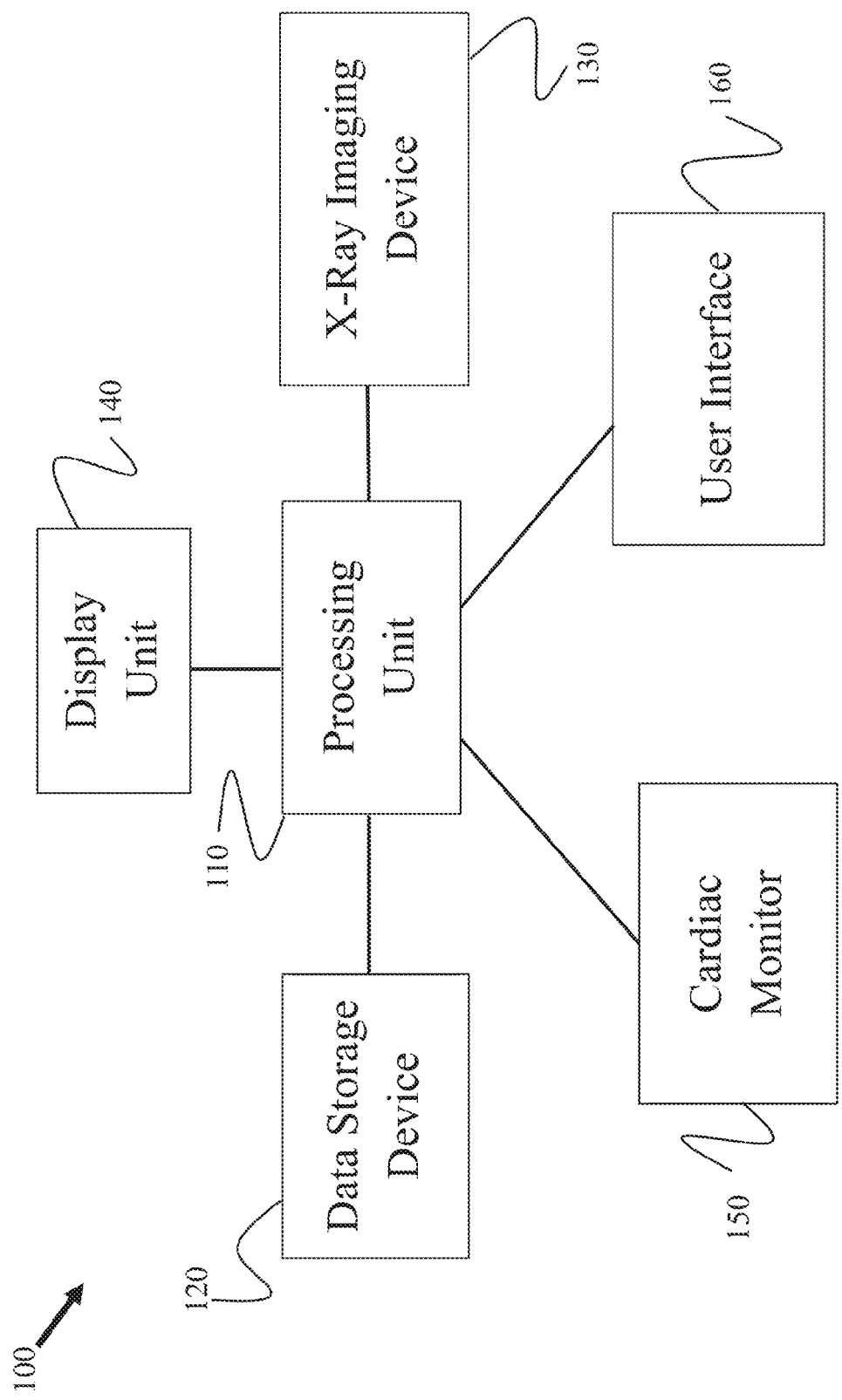
FIG. 7 is a block diagram of a heartbeat synchronized cardiac imaging system in accordance with at least one embodiment of the present technology.

FIG. 7 is a block diagram of one embodiment of a heartbeat synchronized cardiac imaging system 100 that can be used to implement the present technology. In some embodiments, the system 100 can comprise a computer, or a processing unit 110. The processing unit can include, or be in communication with a data storage device 120, an x-ray imaging device 130, a display unit 140, a cardiac monitor 150, and a user interface 160, for example. In this manner, the system 100 can be used to measure a patient's heart rate, synchronize x-ray imaging pulses with the patient's heartbeat, and obtain a series of images at desired states of the cardiac cycle. The images can then be stored in the data storage device 120, and/or displayed via the display unit 140.

The x-ray imaging device 130 can be, for example, a fixed-room c-arm or a mobile c-arm. The x-ray imaging device 130 can be used to obtain x-ray images, for example, cardiac x-ray images. In certain embodiments, the x-ray imaging device can be configured to acquire x-ray images by generating a series of x-ray pulses. The x-ray pulses can occur at a pulse rate (e.g., number of pulses per second) and have a pulse duration (i.e., the length of the pulse).

The cardiac monitor 150 is configured to obtain heartbeat information relating to the cardiac cycle of a patient. In some embodiments, the cardiac monitor 150 monitors a patient's heartbeat, or otherwise obtains a heartbeat reading. The cardiac monitor 150 can be, for example, an ECG unit that obtains a patient's ECG, or another device capable of obtaining heartbeat information. The cardiac monitor 150 can be configured to obtain other information about the patient's heartbeat, for example, in some embodiments the cardiac monitor 150 can be used to identify the peak of the cardiac cycle of the patient's heartbeat.

The system 100 can also comprise a data storage device 120, which can be a computer hard drive, a network, or another storage medium, for example. In this manner, the storage device 120 can be capable of storing x-ray images obtained by the x-ray imaging device and/or processed by the processing unit 110. The data storage device 120 can also be used to store other information, such as information obtained via the cardiac monitor 150, for example.

In some embodiments, the system 100 comprises a user interface 160. The user interface 160 can be configured, for example, to allow a user to operate the x-ray imaging device 130, the cardiac monitor 150, the data storage device 120 and/or the display unit 140. For example, the user interface 160 can provide interactive control software allowing a user to obtain a patient's heartbeat information, to execute imaging functionality, or to access and/or view various x-ray images stored on the data storage device 120.

The processing unit 110 can be a computer processor, for example, that operates various functionality of the system 100. In some embodiments, the processing unit 110 can execute a synchronization application that generates a synchronized pulse rate, for example, based on the heartbeat information of the patient obtained by the cardiac monitor 150.

In some embodiments, the processing unit 110 can also be configured to execute an imaging application that can operate the x-ray imaging device 130. For example, the imaging application can be used to control the pulse rate, the pulse duration, and the pulse distribution of the x-ray imaging device 130. In some embodiments, the imaging application can operate the x-ray imaging device 130 based on a synchronized pulse rate determined by the synchronization application, for example. In this manner, the processing unit 110 can be configured to obtain x-ray images by generating x-ray pulses in the various manners described herein. For example, the processing unit 110 can be configured to generate series of x-ray pulses over various cardiac cycles that are offset or delayed from one another as a way to generate high temporal resolution cardiac images. In additional embodiments, the processing unit 110 can be configured to generate one or multiple x-ray pulses at the same cardiac states over various cardiac cycles so that the images can be combined to generate a higher quality accumulated image.

In some embodiments, for example, the synchronization application can be configured to generate a first synchronized pulse rate to obtain a first set of x-ray images during a first cardiac cycle. The synchronization application can also be configured to generate additional synchronized pulse rates to obtain additional sets of x-ray images during subsequent cardiac cycles. In this manner each x-ray image can be acquired at a relative state of the cardiac cycle of the patient.

The synchronization application can also be configured to implement a relative delay between the first synchronized pulse rate and the additional synchronized pulse rates so that the relative states of the additional sets of x-ray images are offset from the relative states of the first set of x-ray images. For example, the synchronization application can be configured to generate pulse rates and delays in accordance with the example depicted in FIGS. 1 and 2, and described herein.

Additionally and/or alternatively, the synchronization application can configure synchronized pulse rates to generate x-ray images that share common relative states of the cardiac cycle, for example, as depicted in the examples depicted in FIGS. 4, 5, and 6, and described herein.

The processing unit 110 can also be configured to execute an image combination application that combines x-ray images to generate cardiac cycle images. That is, the combination application can be used to generate high temporal resolution cardiac images, and/or accumulated cardiac images as described herein. The combination application can use, for example, one or more of the formulas, equations, and/or algorithms described herein to combine the x-ray images.

In some embodiments, the combination application is configured to arrange the first set of x-ray images and the at least one additional set of images based on the chronological order of the relative states of the x-ray images. For example, the images can be combined in accordance with the examples depicted in FIGS. 1 and 2. Additionally and/or alternatively, the combination application can be configured to add images that share common relative states of the cardiac cycle to generate an accumulated x-ray image.

In certain embodiments, the processing unit can be configured execute a state selection application. For example, the state selection application can be operable via the user interface. In this manner, a user (e.g., a doctor) can be allowed to select a state application allows a user to select a relative state of the cardiac cycle for imaging. In some embodiments, the state selection application, the synchronization application, and the combination application can operate together, such that the synchronization application generates an x-ray pulse at the user-selected state of the cardiac cycle over multiple cardiac cycles. The image combination application can then add images obtained from the x-ray pulses to generate an accumulated image of the heart at the user-selected relative state, for example, as demonstrated by FIG. 6. In some embodiments, the state selection application can allow a user to select a relative state of the cardiac cycle with a control slider application operable via the user interface, for example, as shown in FIGS. 5 and 6.

The x-ray images can be displayed to the user via a display unit 140. The display unit 140 can be, for example, a monitor or other device for displaying digital images, including x-ray images. For example, the display unit 140 can be a monitor connected to one or more of the processing unit 110, the data storage device 120, and the x-ray imaging device 130 and used to visually display the x-ray image.

Figure 8:
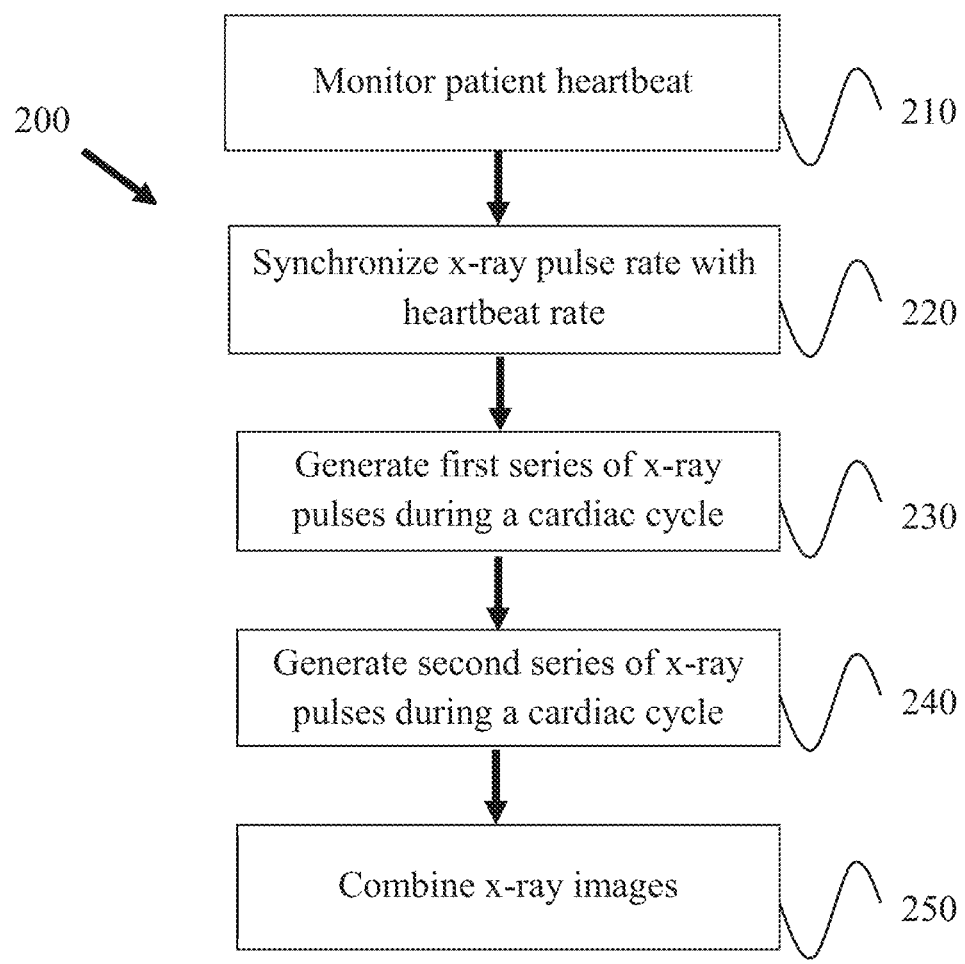
FIG. 8 is a flow diagram of a method for generating cardiac cycle x-ray images in accordance with at least one embodiment of the present technology.

Certain embodiments of the present technology provide methods for generating cardiac cycle x-ray images. FIG. 8 provides a flow diagram of one example of such a method 200.

At step 210, the method 200 monitors the heartbeat rate of a patient. For example, step 210 can involve measuring the heartbeat rate of the patient. In some embodiments, step 210 can include obtaining an ECG reading on a patient's heartbeat. Step 210 can further include obtaining other information about the heartbeat of the patient. For example, at step 210, the peaks defining each of a series of repeating cardiac cycles can be defined. In some embodiments of the present technology, step 210 can be performed by the cardiac monitor 150, and can be controlled by a processor executing instructions involving a routine that is configured to obtain heartbeat information, for example, by obtaining a heartbeat reading.

At step 220, an x-ray pulse rate is synchronized with the heartbeat rate. This can be performed, for example, by a computer processor executing a synchronization application as described herein. In some embodiments, the x-ray pulse rate is generated to obtain a predetermined number of x-ray images per cardiac cycle. The synchronized pulse rate can also be determined, in part, based on the limitations of the x-ray imaging equipment. For example, in some embodiments, an x-ray imaging device may be able to obtain a maximum of 20 PPS. In such a situation, where a heartbeat rate is measured (e.g., at step 210) at 120 beats per second, the x-ray pulse rate can be synchronized at a pulse rate of 10 beats per cardiac cycle. In some embodiments, step 220 can further involve determining a delay, or an offset. For example, where a high temporal resolution cardiac image is desired, step 220 can further include determining a delay such that a number of successive series of x-ray pulses can be generated over successive cardiac cycles to generate x-ray images corresponding to different relative states of the cardiac cycle.

At step 230, a first series of x-ray pulses are generated during a first cardiac cycle to obtain a first set of x-ray images. For example, a processor unit can execute an imaging application that operates an x-ray imaging device to acquire a number of x-ray images over the first cardiac cycle. In some embodiments, the first set of x-ray pulses can be configured such that the first image is acquired at the peak of the cardiac cycle. Successive x-ray pulses can be obtained to occur at regular intervals following the initial x-ray pulse, for example, every 50 ms.

At step 240, a second series of x-ray image pulses are obtained during a second cardiac cycle. In some embodiments, several successive series of x-ray image pulses are obtained over several successive cardiac cycles. The second and successive series of x-ray pulses can be generated at the same pulse rate used in step 230 to obtain the first series of x-ray images. In some embodiments, the second series of x-ray pulses (and other successive series of x-ray pulses) are configured to occur with a delay with respect to the first series of pulses, relative to the cardiac cycle. For example, the second series of x-ray pulses can be configured such that the first pulse of the cycle occurs with a 10 ms delay with respect to the peak of the heartbeat, the third series of x-ray pulses occurring with a 20 ms delay, and so on. The delay can be based, at least in part, on the heartbeat rate and the number of additional sets of images to be acquired. In this manner, a number of x-ray images can be acquired at multiple relative states of the cardiac cycle. In some embodiments, the delay is configured so that the first series of x-ray pulses partially overlap with at least one of the additional series of x-ray pulses.

Additionally and/or alternatively, the x-ray pulses can be configured to occur at the same relative states of the cardiac cycle as those of the first series. In some embodiments of the present technology, steps 230 and 240 can be performed by a computer processor executing instructions involving a routine that is configured to generate a series of x-ray pulses during a plurality of cardiac cycles, each pulse of the series of x-ray pulses configured to occur at a relative state of the cardiac cycle. The instructions can also be configured to adjust the relative state of the cardiac cycle at which each x-ray pulse is generated.

At step 250, the images acquired by x-ray pulses over multiple cardiac cycles are combined. This can be performed, for example, by an image combination application executed by a computer processor or processing unit executing a routine configured to combine x-ray images to generate cardiac cycle images Step 250 can involve combining the first set of x-ray images and the at least one additional set of x-ray images to obtain a cardiac cycle x-ray image. For example, the step of combining can involve arranging the x-ray images based on the chronological order relative states of the cardiac cycle for each x-ray image. In some embodiments, the method can be configured to obtain at least 50 images per cardiac cycle and assembling the images to obtain high temporal resolution cardiac images.

Additionally and/or alternatively, step 250 can involve adding images from the first series of x-ray pulses to images from the second and additional series of x-ray pulses to generate one or more accumulated x-ray images, where each accumulated x-ray image corresponds to a relative state of the cardiac cycle.

In some embodiments, the method 200 can also include the step of selecting a relative state of the cardiac cycle for imaging. This can be performed, for example, by a computer processor executing a state selection application as described herein. For example, a user can be provided with a cardiac selection state slider allowing the user to select a relative state of the cardiac cycle for imaging. In this manner, the method 200 can generate multiple x-ray pulses to occur at the user-selected relative state over multiple cardiac cycles. The heartbeat synchronized imaging system, wherein the combining step adds the x-ray images occurring at the user-selected relative state of the cardiac cycle to generate an accumulated image of the heart at the user-selected relative state.

The present technology has been described with respect to certain techniques, and involving certain equipment. For example, the present technology is described as using a cardiac monitor that obtains ECG readings. It should be noted, however the present technology could also employ other methods for obtaining heartbeat and/or heart rate information such as ultrasound and photoplethysmography, for example.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A heartbeat synchronized imaging system comprising:
   an x-ray imaging device configured to acquire x-ray images by generating a series of x-ray pulses,
   a cardiac monitoring unit configured to obtain heartbeat information relating to the cardiac cycle of a patient;
   a data storage device operable of storing x-ray images obtained by the x-ray imaging device;
   a user interface configured to allow a user to operate at least one of the x-ray imaging device, the cardiac monitoring unit, and the data storage device; and
   a processing unit communicatively coupled to the x-ray imaging device, the cardiac monitoring unit, the data storage device, and the user device, the processing unit configured to:
      execute a synchronization application that generates at least one synchronized constant x-ray pulse rate based on the heartbeat information of the patient;
      execute an imaging application that operates the x-ray imaging device at the at least one synchronized constant x-ray pulse rate across a plurality of cardiac cycles to obtain x-ray images; and
      execute an image combination application that combines x-ray images to generate cardiac cycle images.

2. The heartbeat synchronized imaging system of claim 1, wherein the synchronization application generates a first synchronized constant pulse rate to obtain a first set of x-ray images during a first cardiac cycle, and wherein the synchronization application generates at least one additional synchronized constant pulse rate to obtain at least one additional set of x-ray images during at least one subsequent cardiac cycle, wherein each x-ray image is acquired at a relative state of the cardiac cycle of the patient.

3. The heartbeat synchronized imaging system of claim 2, wherein synchronization application implements a relative delay between the first synchronized constant pulse rate and the at least one additional synchronized constant pulse rate such that the relative states of the at least one additional set of x-ray images is offset from the relative states of the first set of x-ray images.

4. The heartbeat synchronized imaging system of claim 3, wherein the image combination application is configured to arrange the first set of x-ray images and the at least one additional set of x-ray images based on the chronological order of the relative states of the x-ray images.

5. The heartbeat synchronized imaging system of claim 2, wherein the first synchronized constant pulse rate and the at least one additional synchronized constant pulse rate is configured to generate x-ray images with common relative states of the cardiac cycle.

6. The heartbeat synchronized imaging system of claim 5, wherein the image combination application is configured to add images with common relative states of the cardiac cycle to generate an accumulated x-ray image.

7. The heartbeat synchronized imaging system of claim 1, wherein the processing unit is configured to further execute a state selection application operable via the user interface, wherein the state selection application allows a user to select a relative state of the cardiac cycle for imaging.

8. The heartbeat synchronized imaging system of claim 7, wherein the synchronization application generates an x-ray pulse at the user-selected state of the cardiac cycle over a plurality of cardiac cycles, and wherein the image combination application adds images obtained from the x-ray pulses to generate an accumulated x-ray image of the heart at the user-selected relative state.

9. The heartbeat synchronized imaging system of claim 8, wherein the state selection application allows a user to select a relative state of the cardiac cycle with a control application operable via the user interface.

10. A method for generating cardiac cycle x-ray images, the method comprising:
    monitoring a heartbeat to obtain heartbeat information, the heartbeat defined by a repeating cardiac cycle;
    generating a first series of x-ray pulses at a first constant pulse rate during a first cardiac cycle to obtain a first set of x-ray images,
    generating at least one additional series of x-ray pulses at an at least one additional constant pulse rate during at least one subsequent cardiac cycle to obtain at least one additional set of x-ray images; and
    combining the first set of x-ray images and the at least one additional set of x-ray images to obtain a cardiac cycle x-ray image,
    wherein each series of x-ray pulses are configured based on the heartbeat information, and wherein each x-ray pulse generates an x-ray image at a relative state of the cardiac cycle.

11. The method of claim 10, wherein the step of generating at least one additional series of x-ray pulses further comprises instituting a delay so that the x-ray images obtained by the additional series of x-ray pulses have relative states that are offset from the images obtained by the first series of x-ray pulses.

12. The method of claim 11, wherein the step of combining comprises arranging the x-ray images based on the chronological order relative states of the cardiac cycle for each x-ray image.

13. The method of claim 12, wherein the x-ray pulses are configured to obtain x-ray images over at least 50 different relative states of the cardiac cycle.

14. The method of claim 12, wherein the delay is configured so that the first series of x-ray pulses partially overlap with at least one of the additional series of x-ray pulses.

15. The method of claim 12, wherein the length of the delay is based at least in part on the heartbeat information and the number of additional sets of images to be acquired.

16. The method of claim 10, wherein the first series of x-ray pulses and the at least one additional series of x-ray pulses are configured to occur at the same relative states of the cardiac cycle.

17. The method of claim 16, wherein the step of combining comprises adding images from first series of x-ray images to images from the at least one additional series of x-ray images to generate at least one accumulated x-ray image, each accumulated x-ray image corresponding to a relative state of the cardiac cycle.

18. The method of claim 10, further comprising the step of selecting a relative state of the cardiac cycle for imaging, and wherein each series of x-ray pulses comprise one x-ray pulse occurring at the user-selected relative state of the cardiac cycle.

19. The heartbeat synchronized imaging system of claim 18, wherein the combining step adds the x-ray images occurring at the user-selected relative state of the cardiac cycle to generate an accumulated image of the heart at the user-selected relative state.

20. A non-transitory computer-readable medium encoded with a set of instructions for a computer, the instructions comprising:

a first routine configured to obtain heartbeat information, the heartbeat defined by a repeating cardiac cycle;

a second routine configured to generate a series of x-ray pulses at a constant pulse rate during a plurality of cardiac cycles, each pulse of the series of x-ray pulses configured to occur at a relative state of the cardiac cycle; and a third routine configured to adjust the relative state of the cardiac cycle at which each x-ray pulse is generated.

\* \* \* \* \*